US012605105B2

(12) United States Patent
Spangler et al.

(10) Patent No.: US 12,605,105 B2
(45) Date of Patent: Apr. 21, 2026

(54) DIRECTIONAL DILATOR FOR INTRAOPERATIVE MONITORING

(71) Applicant: NuVasive, Inc., San Diego, CA (US)

(72) Inventors: Jonathan D. Spangler, Del Mar, CA (US); Forrest Samuel, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 988 days.

(21) Appl. No.: 17/721,965

(22) Filed: Apr. 15, 2022

(65) Prior Publication Data

US 2022/0233121 A1     Jul. 28, 2022

Related U.S. Application Data

(60) Division of application No. 15/881,624, filed on Jan. 26, 2018, now Pat. No. 11,337,630, which is a continuation of application No. 13/830,508, filed on Mar. 14, 2013, now Pat. No. 9,888,859.

(60) Provisional application No. 61/612,195, filed on Mar. 16, 2012.

(51) Int. Cl.
| | |
|---|---|
| *A61B 5/24* | (2021.01) |
| *A61B 5/00* | (2006.01) |
| *A61B 5/389* | (2021.01) |

(52) U.S. Cl.
CPC ................ *A61B 5/24* (2021.01); *A61B 5/389* (2021.01); *A61B 5/4893* (2013.01)

(58) Field of Classification Search
None
See application file for complete search history.

(56) References Cited

U.S. PATENT DOCUMENTS

| | | |
|---|---|---|
| 208,227 A | 9/1878 | Dorr |
| 972,983 A | 10/1910 | Arthur |
| 1,328,624 A | 1/1920 | Graham |
| 4,545,374 A | 10/1985 | Jacobson |
| 4,573,448 A | 3/1986 | Kambin |
| 4,630,611 A | 12/1986 | King |
| 5,007,902 A | 4/1991 | Witt |
| 5,171,279 A | 12/1992 | Mathews |
| 5,295,994 A | 3/1994 | Bonutti |
| 5,312,417 A | 5/1994 | Wilk |
| 5,331,975 A | 7/1994 | Bonutti |
| 5,342,384 A | 8/1994 | Sugarbaker |
| 5,378,241 A | 1/1995 | Haindl |
| 5,395,317 A | 3/1995 | Kambin |
| 5,509,893 A | 4/1996 | Pracas |
| 5,514,153 A | 5/1996 | Bonutti |
| 5,599,279 A | 2/1997 | Slotman et al. |
| 5,707,359 A | 1/1998 | Bufalini |
| 5,762,629 A | 6/1998 | Kambin |
| 5,792,044 A | 8/1998 | Foley et al. |
| 5,814,073 A | 9/1998 | Bonutti |
| 5,817,071 A | 10/1998 | Dewindt et al. |
| 5,888,196 A | 3/1999 | Bonutti |

(Continued)

*Primary Examiner* — Matthew Kremer

(57) ABSTRACT

A stationary dilator has one or more electrodes in the distal region that are rotatable around the longitudinal axis of the dilator. The one or more electrodes are operable to deliver electrical stimulation signals to tissue through which the dilator is passed. The stimulation signals can be used for determining nerve directionality and optionally nerve proximity during surgical procedures involving the presence of neural structures.

14 Claims, 13 Drawing Sheets

(56) References Cited

U.S. PATENT DOCUMENTS

| | | | |
|---|---|---|---|
| 5,902,231 A | 5/1999 | Foley et al. | |
| 5,976,146 A | 11/1999 | Ogawa et al. | |
| 6,007,487 A | 12/1999 | Foley et al. | |
| 6,010,520 A | 1/2000 | Pattison | |
| 6,146,371 A | 11/2000 | Dewindt et al. | |
| 6,152,871 A | 11/2000 | Foley et al. | |
| 6,159,179 A | 12/2000 | Simonson | |
| 6,161,047 A | 12/2000 | King et al. | |
| 6,206,826 B1 | 3/2001 | Mathews et al. | |
| 6,217,509 B1 | 4/2001 | Foley et al. | |
| 6,217,527 B1 | 4/2001 | Selmon et al. | |
| 6,221,049 B1 | 4/2001 | Selmon et al. | |
| 6,231,546 B1 | 5/2001 | Milo et al. | |
| 6,245,082 B1 | 6/2001 | Gellman et al. | |
| 6,270,505 B1 | 8/2001 | Yoshida et al. | |
| 6,292,701 B1 | 9/2001 | Prass et al. | |
| 6,325,764 B1 | 12/2001 | Griffith et al. | |
| 6,395,007 B1 | 5/2002 | Bhatnagar et al. | |
| 6,425,859 B1 | 7/2002 | Foley et al. | |
| 6,447,484 B1 | 9/2002 | Briscoe et al. | |
| 6,514,217 B1 | 2/2003 | Selmon et al. | |
| 6,520,907 B1 | 2/2003 | Foley et al. | |
| 6,529,774 B1 | 3/2003 | Greene | |
| 6,535,759 B1 | 3/2003 | Epstein et al. | |
| 6,564,078 B1 | 5/2003 | Marino et al. | |
| 6,641,613 B2 | 11/2003 | Sennett | |
| 6,645,194 B2 | 11/2003 | Briscoe et al. | |
| 6,679,833 B2 | 1/2004 | Smith et al. | |
| 6,711,430 B1 | 3/2004 | Ferris et al. | |
| 6,719,692 B2 | 4/2004 | Kleffner et al. | |
| 6,847,849 B2 | 1/2005 | Mamo et al. | |
| 6,855,105 B2 | 2/2005 | Jackson, III | |
| 6,916,330 B2 | 7/2005 | Simonson | |
| 6,926,728 B2 | 8/2005 | Zucherman et al. | |
| 6,929,606 B2 | 8/2005 | Ritland | |
| 6,997,941 B2 | 2/2006 | Sharkey et al. | |
| 7,008,431 B2 | 3/2006 | Simonson | |
| 7,074,226 B2 | 7/2006 | Roehm, III et al. | |
| 7,079,883 B2 | 7/2006 | Marino et al. | |
| 7,083,625 B2 | 8/2006 | Berry | |
| 7,198,598 B2 | 4/2007 | Smith et al. | |
| 7,207,949 B2 | 4/2007 | Miles et al. | |
| 7,226,451 B2 | 6/2007 | Shluzas et al. | |
| 7,276,055 B2 | 10/2007 | Dewindt et al. | |
| 7,311,719 B2 | 12/2007 | Bonutti | |
| 7,470,236 B1 | 12/2008 | Kelleher et al. | |
| 7,582,058 B1 | 9/2009 | Miles et al. | |
| 7,819,801 B2 * | 10/2010 | Miles | A61B 1/32 |
| | | | 600/210 |
| 7,905,840 B2 | 3/2011 | Pimenta et al. | |
| 7,920,922 B2 | 4/2011 | Gharib et al. | |
| 7,962,191 B2 | 6/2011 | Marino et al. | |
| 8,000,782 B2 | 8/2011 | Gharib et al. | |
| 8,265,744 B2 | 9/2012 | Gharib et al. | |
| 9,888,859 B1 | 2/2018 | Spangler et al. | |
| 2001/0056280 A1 | 12/2001 | Underwood et al. | |
| 2002/0010392 A1 | 1/2002 | Desai | |
| 2003/0139648 A1 | 7/2003 | Foley et al. | |
| 2004/0081231 A1 | 4/2004 | Kim | |
| 2005/0004593 A1 | 1/2005 | Simonson | |
| 2006/0052669 A1 | 3/2006 | Hart | |
| 2006/0052828 A1 | 3/2006 | Kim et al. | |
| 2006/0058743 A1 | 3/2006 | Putz | |
| 2006/0206178 A1 | 9/2006 | Kim | |
| 2007/0066977 A1 | 3/2007 | Assell et al. | |
| 2007/0083161 A1 | 4/2007 | Briscoe et al. | |
| 2007/0213584 A1 | 9/2007 | Kim et al. | |
| 2008/0021463 A1 | 1/2008 | Georgy | |
| 2009/0069709 A1 | 3/2009 | Schmitz et al. | |
| 2009/0203989 A1 * | 8/2009 | Burnside | A61B 5/06 |
| | | | 600/409 |
| 2009/0259108 A1 * | 10/2009 | Miles | A61B 17/025 |
| | | | 600/202 |
| 2010/0114075 A1 | 5/2010 | Simonton et al. | |
| 2011/0208226 A1 | 8/2011 | Fatone et al. | |
| 2011/0301665 A1 | 12/2011 | Mercanzini et al. | |
| 2014/0114168 A1 | 4/2014 | Block et al. | |

* cited by examiner

DIRECTIONAL DILATOR FOR INTRAOPERATIVE MONITORING

CROSS-REFERENCE TO RELATED APPLICATIONS

This application is a divisional of U.S. patent application Ser. No. 15/881,624 filed Jan. 26, 2018, which is a continuation of U.S. patent application Ser. No. 13/830,508 filed Mar. 14, 2013, now U.S. Pat. No. 9,888,859 issued Feb. 13, 2018, which claims priority to U.S. Provisional Application Ser. No. 61/612,195, filed Mar. 16, 2012 and titled "Stationary Directional Dilators", the complete disclosure of which is hereby incorporated by reference into this application as if set forth fully herein.

BACKGROUND OF THE INVENTION

I. Field of the Invention

The present invention relates generally to surgery and, more particularly, to directional dilation during intraoperative monitoring through the use of a stationary directional dilator.

II. Discussion of the Prior Art

Intraoperative monitoring is commonly employed during surgeries which involve passing surgical instruments near or through tissues or areas having neural structures which, if contacted, may result in neurological deficit for the patient. Spine surgery is but one example and may be employed to address any number of different spinal disorders. To do so, it is necessary to create an operative corridor extending between an incision site and the spinal column. Depending on the approach or trajectory to the spine (e.g. anterior, posterior, lateral, etc.), different tissues will need to be traversed in order to establish the operative corridor.

The XLIF® procedure by NuVasive, Inc. is an exemplary surgical procedure, which involves establishing an operative corridor from a lateral approach to the lumbar spine while traversing through the psoas muscle. The psoas muscle is known to contain nerve roots which exit from the spinal cord. To safely establish an operative corridor through the psoas muscle, Nu Vasive, Inc. has developed certain systems and methods, such as that shown and described in U.S. Pat. No. 7,905,840 (hereinafter "the'840 patent"), the entire content of which is hereby expressly incorporated by reference into this disclosure as if set forth fully herein.

The '840 patent includes an electromyographic (EMG) intraoperative monitoring system and an access system comprising sequential dilators and a split-blade retractor, which collectively provide the ability to establish a so-called "less invasive" or "minimally disruptive" operative corridor through the psoas muscle to a surgical target site in the lumbar spine. Each sequential dilator has an electrode at the distal end which, when coupled to the intraoperative monitoring system, provides the ability to send a stimulation signal into the surrounding tissue to help determine the presence of nerves. Each sequential dilator may be physically rotated about its longitudinal axis during such stimulation to help determine the direction of the nerve(s) relative to the electrode and thus the dilator. This nerve proximity and nerve direction information may be used by the surgeon to help inform his or her surgical decision-making.

The present invention presents an alternate manner of directional dilation during surgeries involving intraoperative monitoring, including but not limited to spine surgery.

SUMMARY OF THE INVENTION

The present invention accomplishes this goal by providing a stationary directional dilator. In one aspect, the stationary directional dilator includes a stationary dilator and a rotatable electrode at the distal end of the stationary dilator. By "stationary" it is meant that during the process of nerve detection the dilator is maintained in a generally static or still position relative to any rotation about its longitudinal axis. In use with an intraoperative monitoring system, a surgeon may hold the stationary dilator in this stationary, "non-rotating" manner while rotating the electrode to detect the presence and/or direction of surrounding nerves during the process of advancing the dilator through tissue towards the surgical target site (e.g., the intervertebral disc in the case of lateral, trans-psoas spinal fusion surgery). This nerve proximity and nerve direction information may, in turn, be used by the surgeon to help inform his or her surgical decision-making.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The stationary directional dilator and associated methods disclosed herein boast a variety of inventive features and components that warrant patent protection, both individually and in combination.

Figures 1, 2:
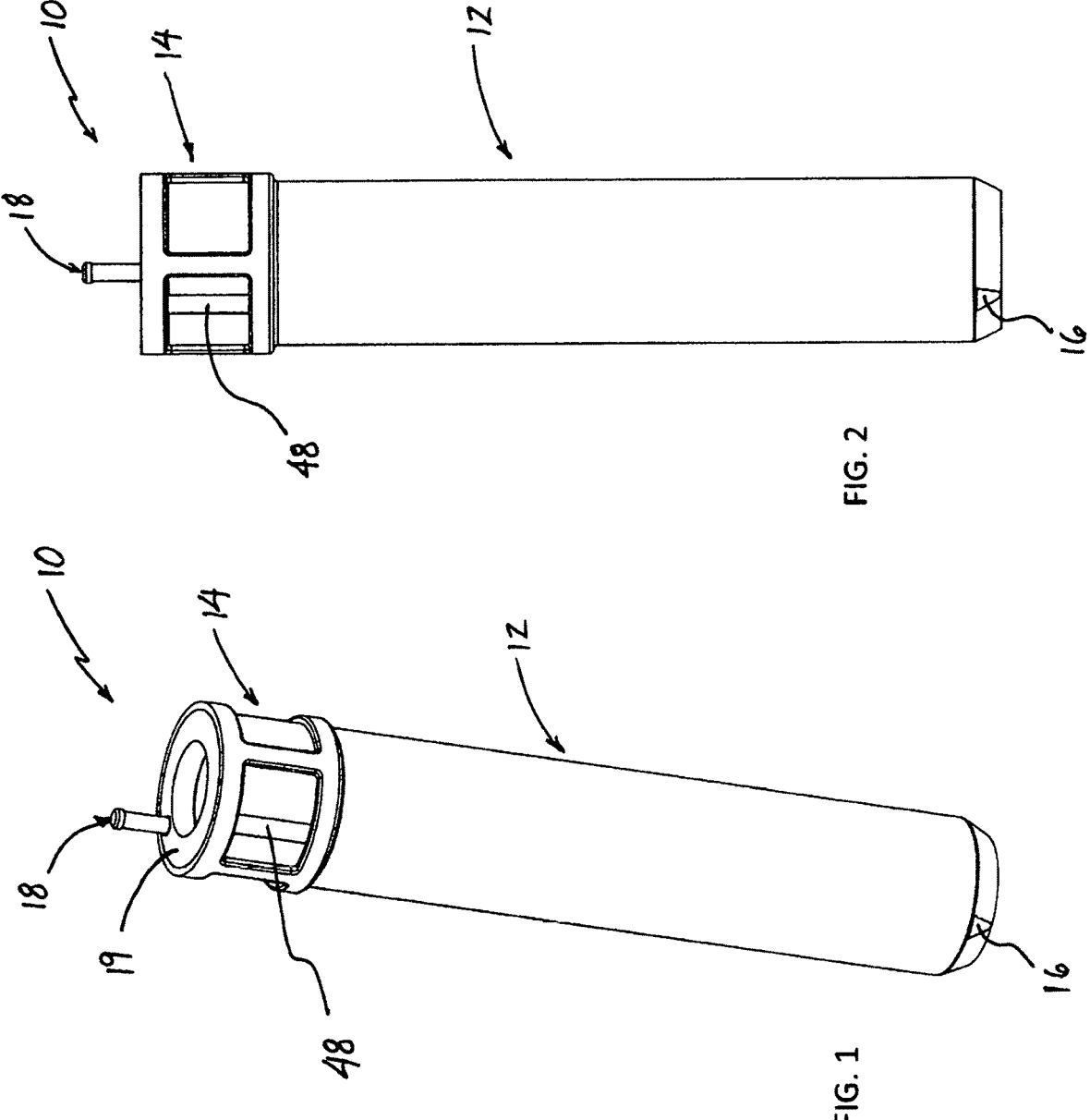
FIGS. 1-2 are perspective and front views, respectively, of a stationary directional dilator according to one aspect of the present invention.

FIGS. 1 and 2 illustrate, by way of example only, a stationary directional dilator 10 according to one aspect of the present invention. The stationary directional dilator 10 includes a stationary dilator 12 and a rotatable electrode structure 14 with an electrode 16 at the distal end. By "stationary" it is meant that the dilator 12 is maintained in a generally static or still position relative to any rotation about its longitudinal axis. The rotatable electrode structure 14 includes an electrode marker 48 located towards the proximal end of the electrode structure 14, which is in alignment with the electrode 16 located at the distal end of the electrode structure 14. An electrical coupler 18 extends from a cap member 19 and is electrically connected to the electrode 16. The electrical coupler 18 is intended to be connected to an intraoperative monitoring system of the type shown and described in the '840 patent. As will be described in greater detail below, the cap member 19 is used to help couple the rotatable electrode structure 14 and the stationary dilator 12 to enable the selective rotation of the electrode structure 14 (and with it electrode 16) relative to the stationary dilator 12.

When coupled to an intraoperative monitoring system, the stationary directional dilator 10 of the present invention may be used to detect the presence and/or direction of surrounding nerves during the process of advancing the dilator 10 through tissue towards the surgical target site. More specifically, the intraoperative monitoring system accomplishes this by sending electrical stimulation signals to the electrode 16 on the stationary directional dilator 10. Depending upon the location of the stationary directional dilator 10 within a patient (and more particularly, to any neural structures), the stimulation signals may cause nerves adjacent to or in the general proximity of the dilator 10 to depolarize. This causes muscle groups to innervate and generate EMG responses, which can be sensed via the EMG electrodes on the legs of the patient. By monitoring these myotomes associated with the nerves and assessing the resulting EMG responses, the intraoperative monitoring system is capable of detecting the presence of such nerves.

To determine the direction to the nerves, the user need simply hold the dilator 12 in a generally stationary position while rotating the electrode 16 as the stimulation signal is being emitted to the surrounding tissue. The closer the nerve is to the electrode 16, the lower the electrical stimulation (e.g. current) required to innervate the nerve. As such, the user may simply rotate the electrode 16 to identify the point in its rotation relative to the dilator 12 at which the stimulation signal required to innervate the nerve is the lowest. This may be accomplished by visualizing graphical indicia (e.g. numbers, colors, etc. . . . ) indicative of the stimulation signal level and/or listening to sounds generated by the intraoperative monitoring system indicative of the stimulation signal level. This point is the direction of the nerve relative to the stationary dilator 12. The electrode marker 48 may be used to help determine the location of the nerve to the stationary dilator 12, given that the electrode 16 will be located within the patient and thus not readily visible.

Figures 3, 4:
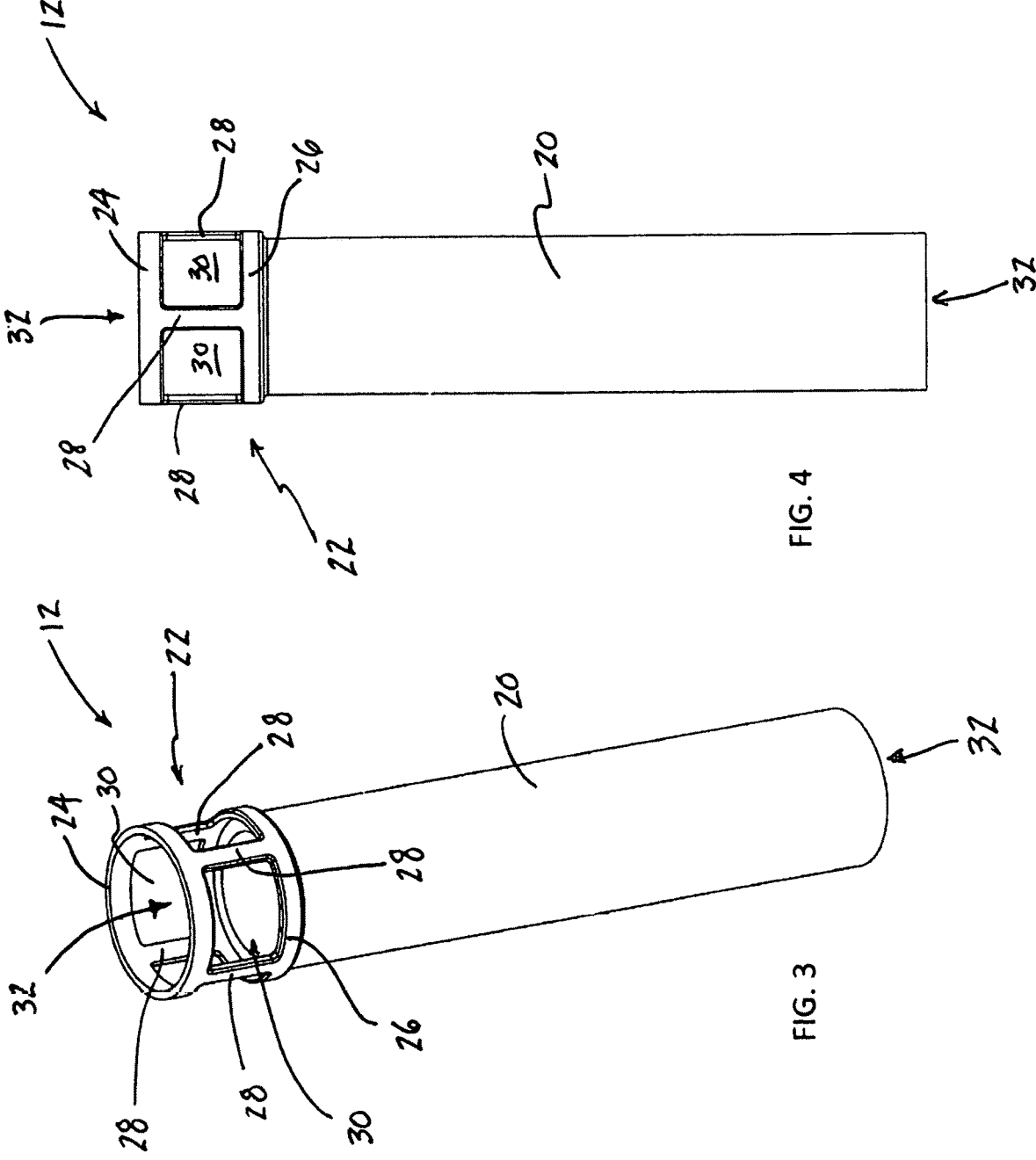
FIGS. 3-4 are perspective and front views, respectively, of an outer dilator forming part of the stationary directional dilator of FIG. 1.

FIGS. 3 and 4 detail the stationary outer dilator 12 forming part of the stationary directional dilator 10 of FIG. 1. The outer dilator 12 includes a generally elongated lower or distal section 20 extending away from an upper or proximal section 22. The proximal section 22 includes an upper ring member 24, a lower ring member 26, and a plurality of struts 28 extending between the upper and lower ring members 24, 26. A plurality of openings 30 are defined between the struts 28 and the upper and lower ring members 24, 26. The distal section 20 and proximal section 22 are both generally tubular and hollow in construction with a contiguous lumen 32 extending through both sections 20, 22. The diameter of the lumen 32 is slightly wider in the proximal section 22 than in the distal section 20, which (as will be described in greater detail below) is designed to accommodate and enable rotation of the proximal end of the rotatable electrode structure 14 (described below).

Figures 5, 6:
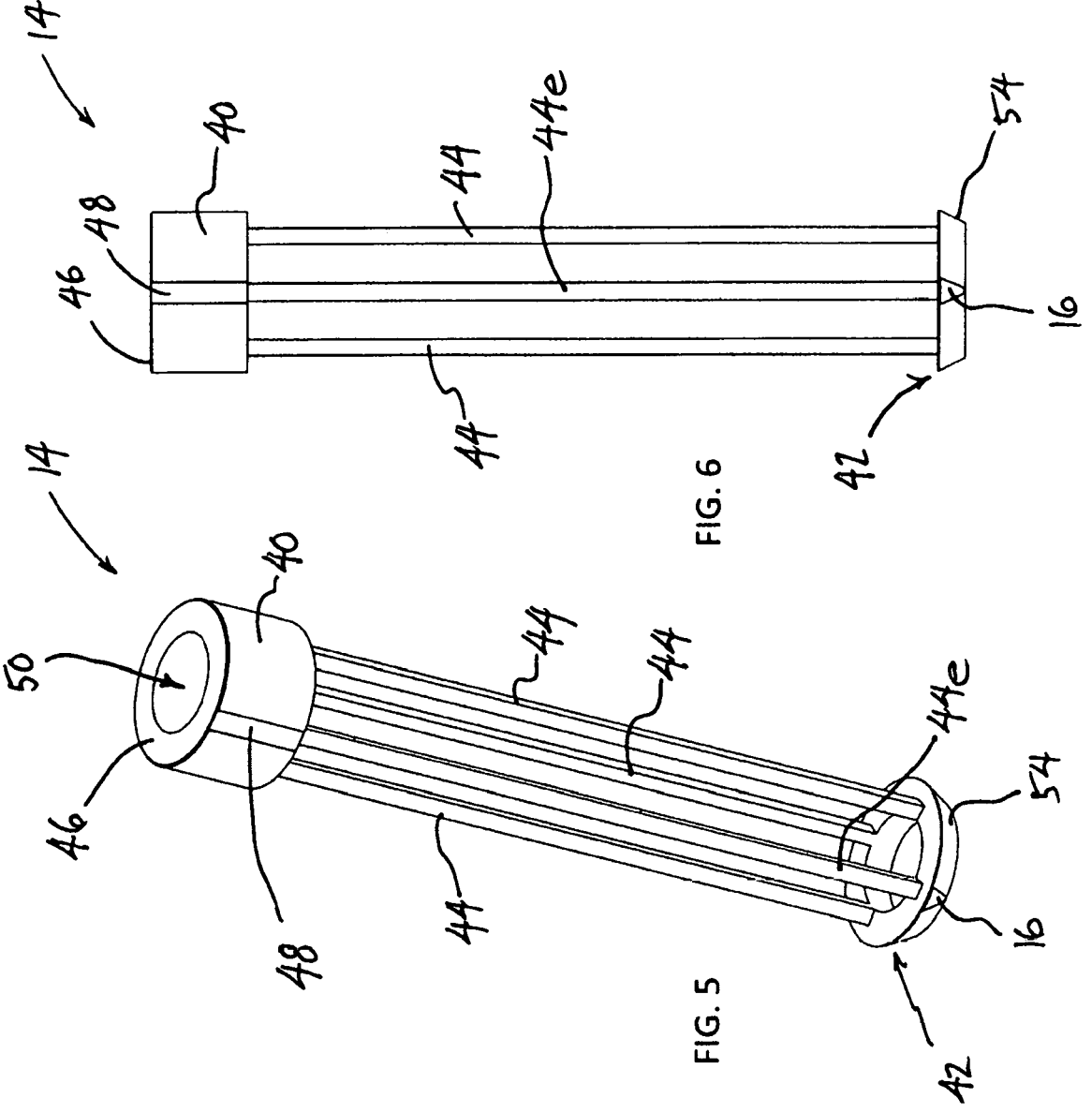
FIGS. 5-6 are perspective and front views, respectively, of a rotatable electrode structure forming part of the stationary directional dilator of FIG. 1.
Figure 8:
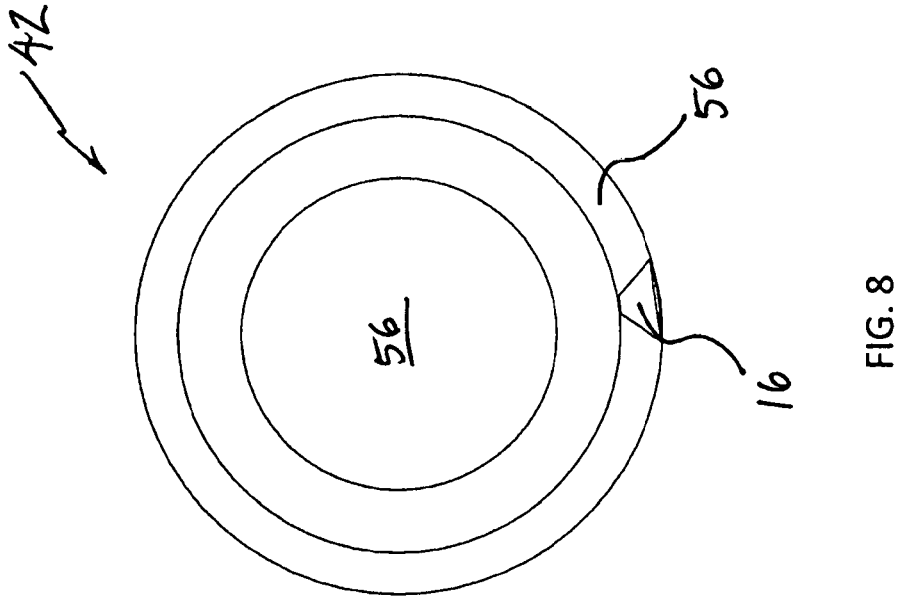
FIGS. 7-8 are top and bottom views, respectively, of the rotatable electrode structure of FIG. 5.
Figure 7:
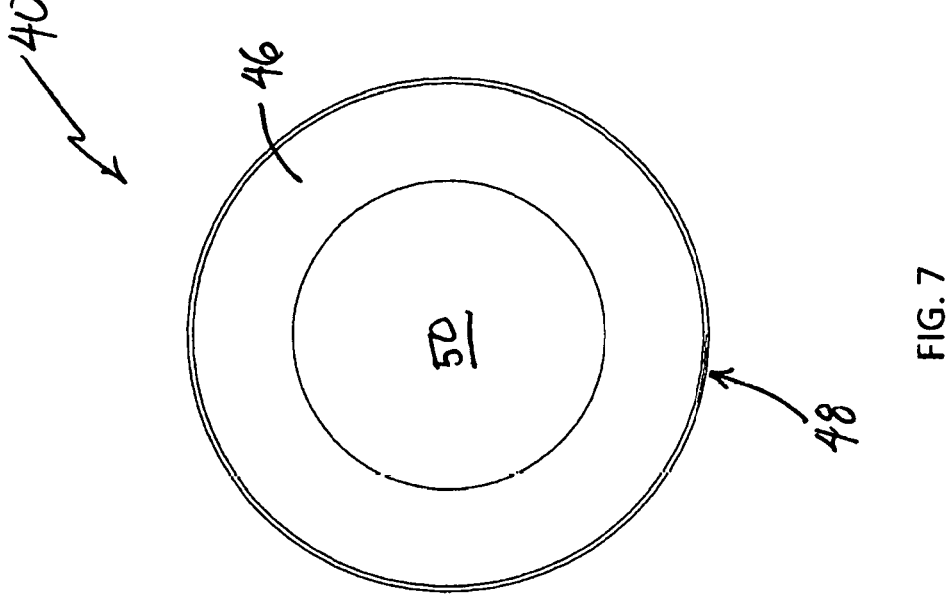

FIGS. 5 and 6 detail the rotatable electrode structure 14 forming part of the stationary directional dilator 10 of FIG. 1. The rotatable electrode structure 14 includes an upper collar member 40, a lower ring member 42, and a plurality of struts 44 extending there between. With combined reference to FIGS. 5-7, the upper collar member 40 includes an upper electrode surface 46, the electrode marker 48, and a lumen 50 extending there through. With combined reference to FIGS. 5-6 and 8, the lower ring member 42 includes electrode 16 disposed on a beveled surface 54, and a lumen 56 extending there through. The diameter of the lumen 50 and the diameter of the lumen 56 are preferably the same or approximately so. This will permit the stationary directional dilator 10 of the present invention to be slidably advanced over a previously placed dilator having an outer diameter slightly less than the inner diameter of the stationary directional dilator 10. It will be appreciated that any such previously placed dilator may be a standard dilator (i.e. without electrodes), an electrified dilator of the type shown (by way of example only) in the '840 patent, or a stationary directional dilator 10 of the present invention only having a smaller outer diameter than shown in the Figures. It will also be appreciated that the dilator 10 may also be dimensioned larger than shown so as to serve as a subsequent dilator within a series of sequential dilators.

The upper electrode surface 46 is electrically coupled to the electrode 16, which may be accomplished in any number of suitable manners. By way of example only, this may be accomplished through the use of an electrical wire or lead extending through and/or along the strut 44e (for "electrical") which is in alignment between the electrode marker 48 and the electrode 16. During use the electrode surface 46 will be brought into electrical communication with the intraoperative monitoring system through the use of the electrical coupler 18 of FIG. 1. Based on the electrical communication between the electrode surface 46 and the electrode 16, then, the electrode 16 will be in communication with the intraoperative monitoring system which, as described above, may be used to detect the presence and/or direction of surrounding nerves during the process of advancing the dilator 10 through tissue towards the surgical target site.

Figures 9, 10:
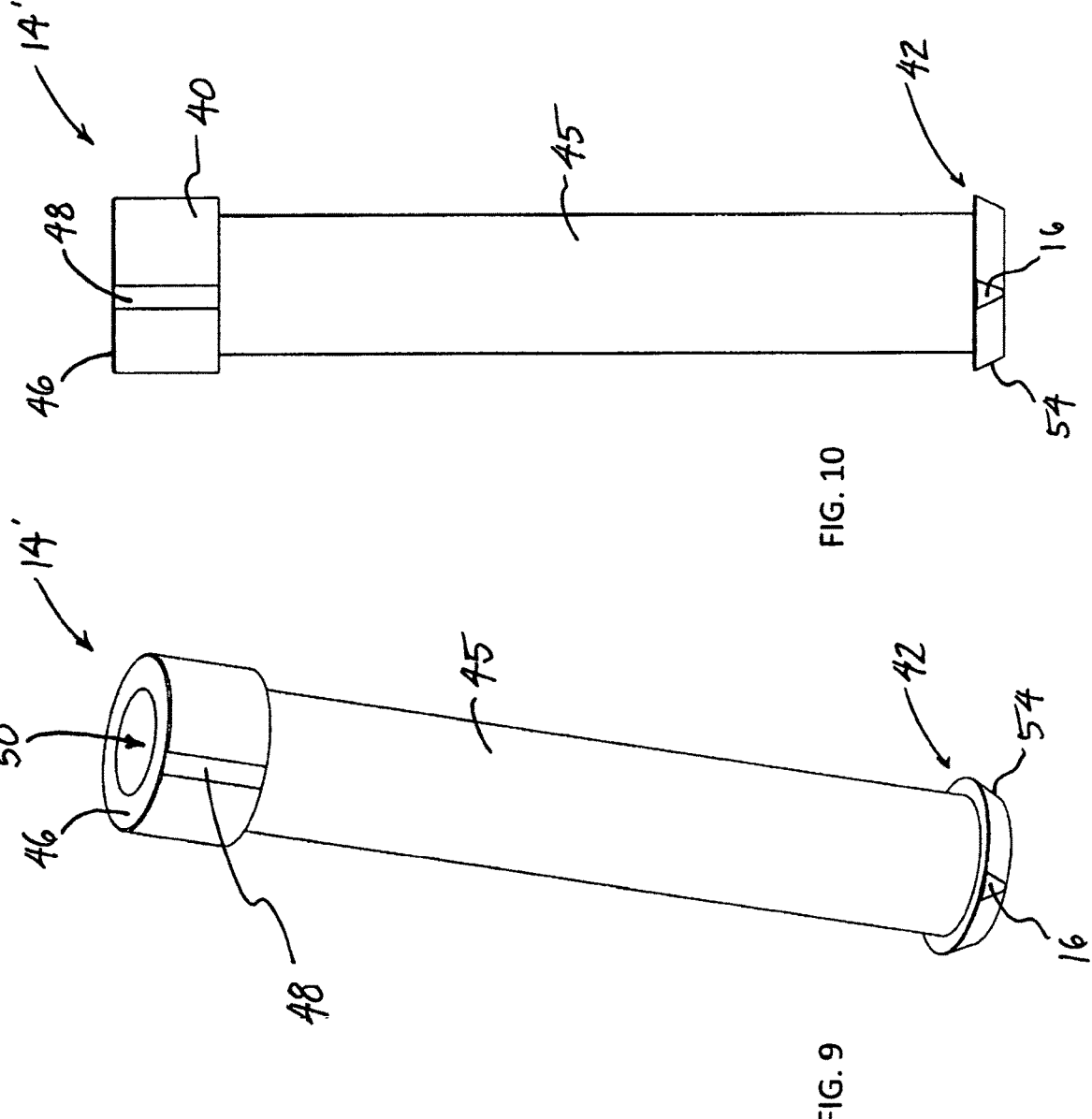
FIGS. 9-10 are perspective and front views, respectively, of a rotatable electrode structure according to an alternate aspect forming part of the stationary directional dilator of FIG. 1.

FIGS. 9-10 detail a rotatable electrode structure 14' according to alternate aspect of the present invention. Based on the commonality of construction and components, and for the sake of brevity, only those features and functions varying from the rotatable electrode structure 14 of FIGS. 5-6 will be described. Electrode structure 14' is virtually identical to that shown in FIGS. 5-6, except that a generally tubular and hollow section 45 replaces the struts 44. In this embodiment, an electrical wire or lead for connecting the surface electrode 46 and the electrode 16 may extend through and/or along the hollow section 45. During use the electrode surface 46 will be brought into electrical communication with the intraoperative monitoring system through the use of the electrical coupler 18 of FIG. 1. Based on the electrical communication between the electrode surface 46 and the electrode 16, the electrode 16 will be in communication with the intraoperative monitoring system which, as described above, may be used to detect the presence and/or direction of surrounding nerves during the process of advancing the dilator 10 through tissue towards the surgical target site.

Figures 11, 12, 13:
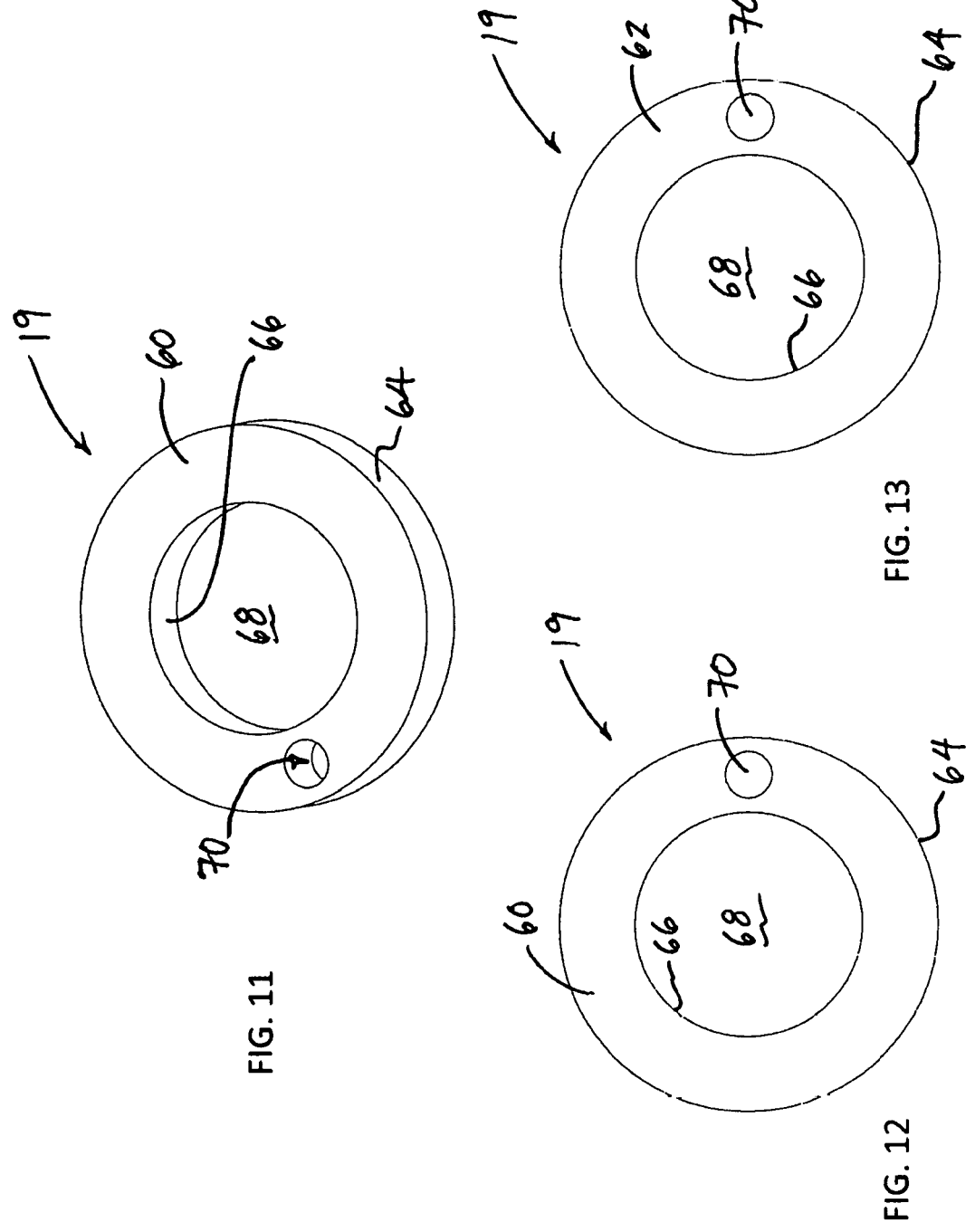
FIGS. 11-13 are perspective, top and bottom views, respectively, of a cap member forming part of the stationary directional dilator of FIG. 1.

FIGS. 11 through 13 detail the cap member 19 forming part of the stationary directional dilator 10 of FIG. 1. The cap member 19 includes an upper surface 60, a lower surface 62, an outer side wall 64, an inner side wall 66, and a central lumen 68 extending between the supper and lower surfaces 60, 62. The diameter of the central 68 is preferably the same (or approximately so) as the diameter of the lumens 50, 56 of the rotatable electrode structure 14. As described above, this permits the stationary directional dilator 10 of the present invention to be slidably advanced over a previously placed dilator having an outer diameter slightly less than the inner diameter of the stationary directional dilator 10. It will be appreciated that any such previously placed dilator may be a standard dilator (i.e. without electrodes), an electrified dilator of the type shown (by way of example only) in the '840 patent, or a stationary directional dilator 10 of the present invention only having a smaller outer diameter than shown in the Figures. The cap member 19 also includes an offset lumen 70 extending between the upper and lower surfaces 60, 62. The offset lumen 70 is dimensioned to receive the electrical coupler 18, which will be described in greater detail below. The upper and lower surfaces 60, 62 are preferably insulated and/or constructed from non-conductive material (e.g. plastic) such that any electricity flowing through the electrical connector 18 during use will not shunt or otherwise become misdirected to other components, the patient, or the surgeon.

Figure 15:
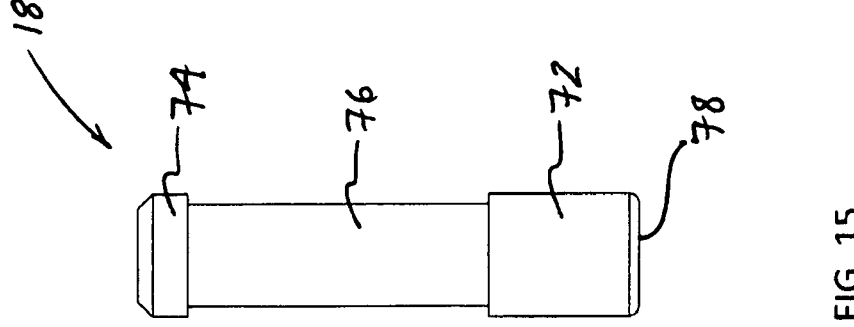
FIGS. 14-15 are perspective and front views, respectively, of an electrical coupling element forming part of the stationary directional dilator of FIG. 1.
Figure 14:
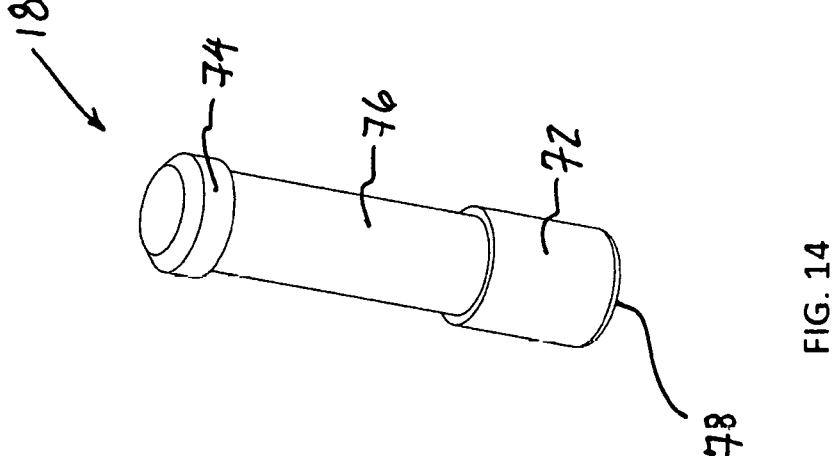

FIGS. 14 and 15 detail the electrical coupling element 18 forming part of the stationary directional dilator 10 of FIG. 1. The electrical coupling element 18 includes a lower region 72, an upper region 74, and a middle region 76. The lower region 72 is dimensioned to be received at least partially within the offset lumen 70 of the cap member 19 and includes a lower surface 78. The lower surface 78 is dimensioned such that, in use, it will be brought into physical (and thus electrical) contact with the upper electrode surface 46 of the collar member 40 of the rotatable electrode structure 14. The middle region 76 is dimensioned to be coupled to a clip or other electrical connector of the type shown and described in the '840 patent for the purpose of establishing electrical communication between the electrical coupler 18 and the intraoperative monitoring system such as that shown in the '840 patent. The middle region 76 has a slightly reduced diameter relative to that of the upper region 75, which serves to prevent such an electrical clip or connector (not shown) from inadvertently disengaging from the electrical coupler 18 as may otherwise occur if it did not include the "stop" formed by the upper region 75.

Figures 16, 17:
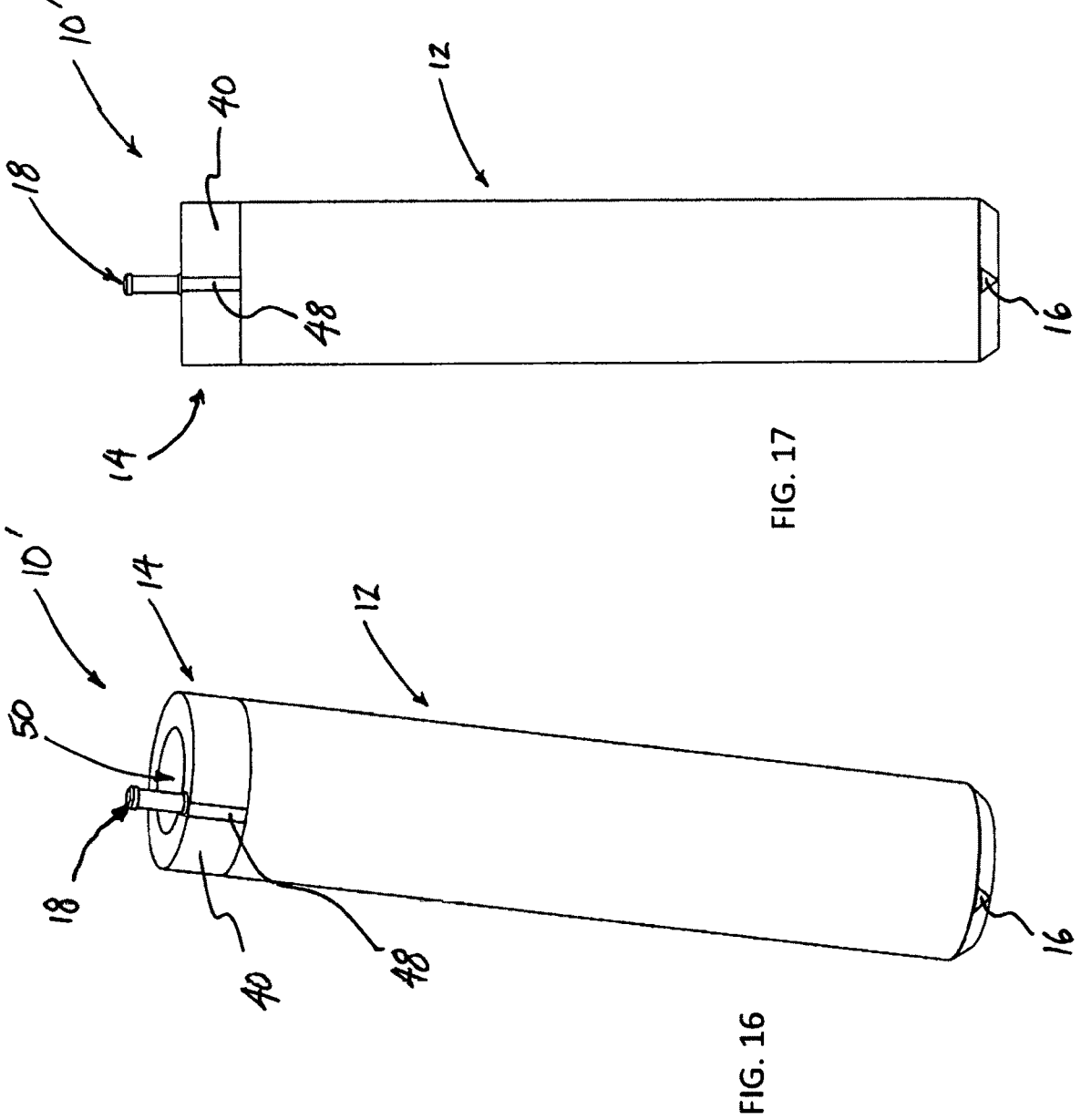
FIGS. 16-17 are perspective and front views, respectively, of a stationary directional dilator according to an alternate aspect.
Figure 19:
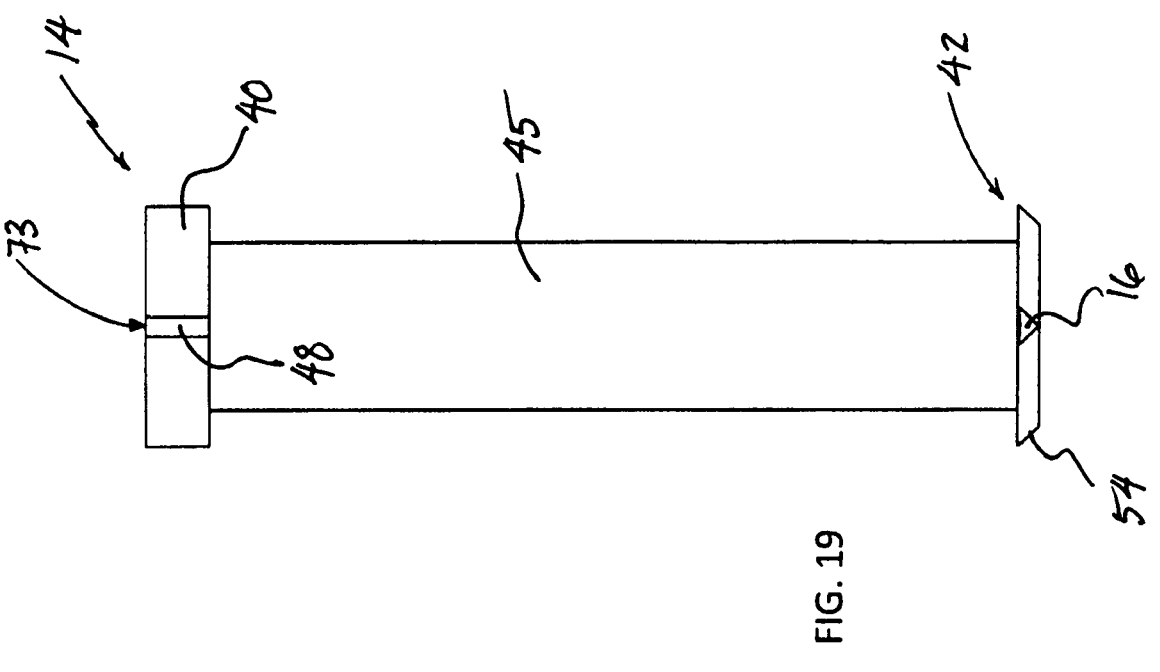
FIGS. 18-19 are perspective and front views, respectively, of a rotatable electrode structure forming part of the stationary directional dilator of FIGS. 16-17.
Figure 18:
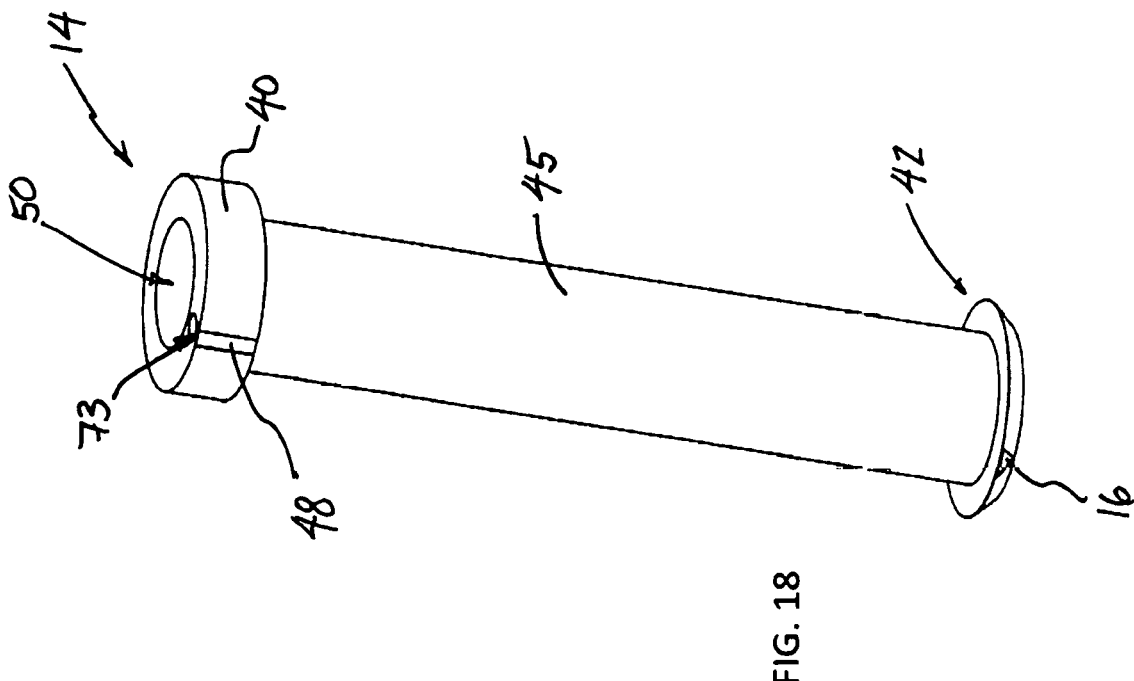

FIGS. 16-17 illustrate, by way of example only, a stationary directional dilator 10' according to another aspect of the present invention. The stationary directional dilator 10' includes a stationary dilator 12 and a rotatable electrode structure 14 with an electrode 16 at the distal end. The outer dilator 12 is generally tubular and hollow along its entire length (it does not include any proximal section 22 as found in FIGS. 1-4) with an inner lumen (not shown, but the same as lumen 32 in FIGS. 3-4) designed to accommodate and enable rotation of the rotatable electrode structure 14. As shown in FIGS. 18-19, the rotatable electrode structure 14 is essentially identical to the embodiment shown and described above with reference to FIGS. 9-10, with the exception that the collar member 40 receives the electrical coupler 18 in an offset lumen 73. In the interest of brevity, the common features and components need not be repeated.

Figures 20, 21:
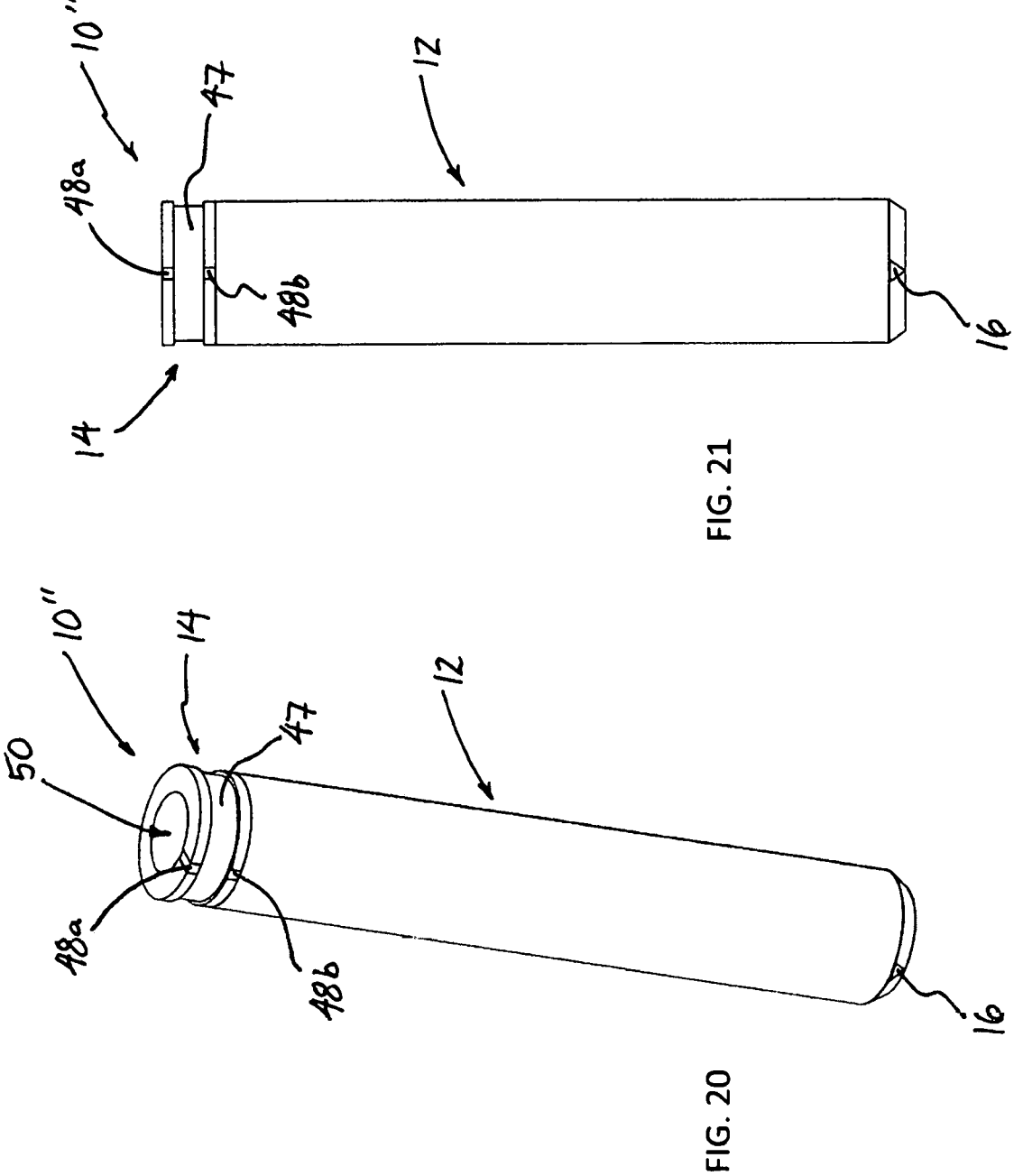
FIGS. 20-21 are perspective and front views, respectively, of a stationary directional dilator according to an alternate aspect.
Figures 22, 23:
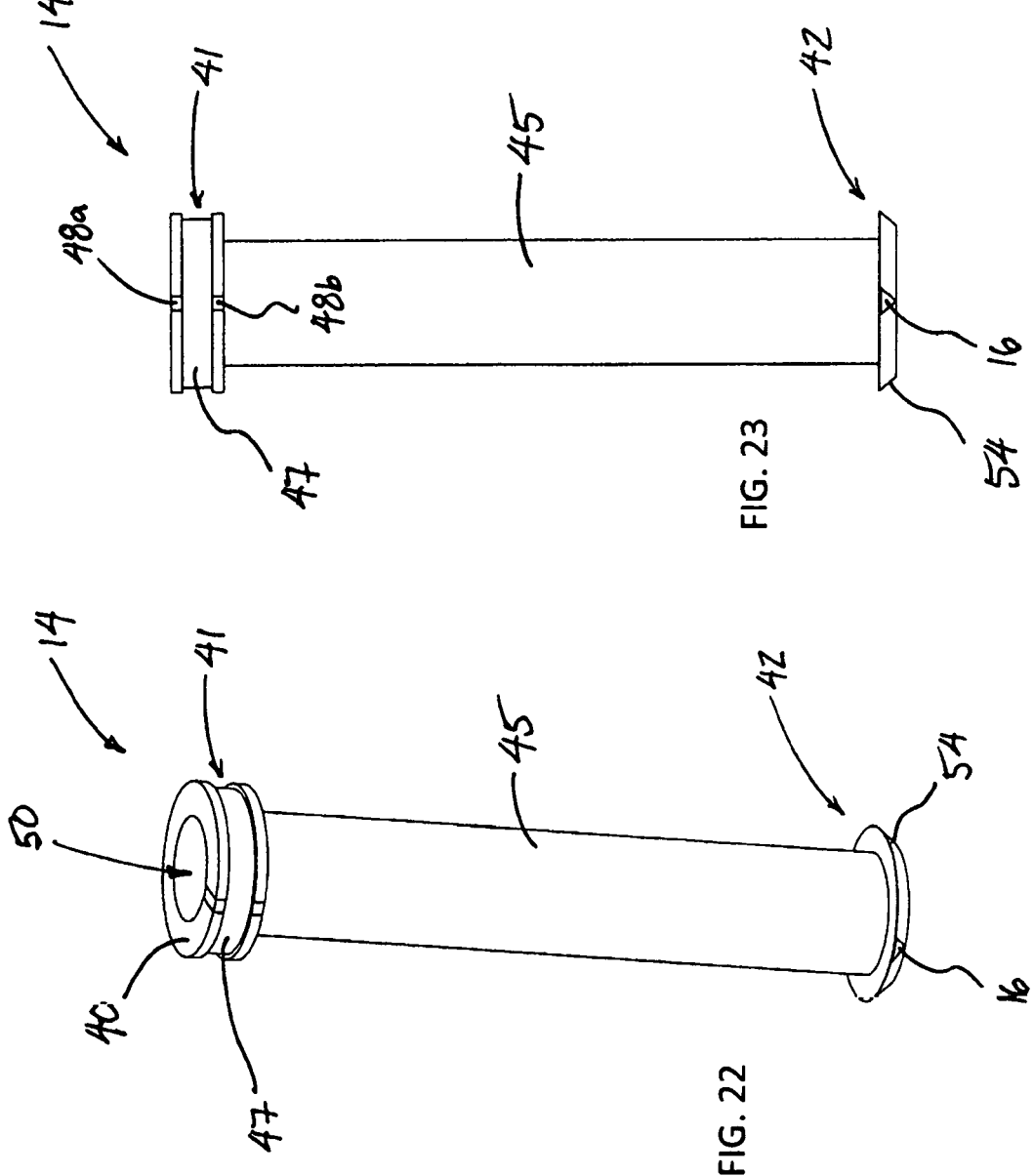
FIGS. 22-23 are perspective and front views, respectively, of a rotatable electrode structure forming part of the stationary directional dilator of FIGS. 20-21.

FIGS. 20-21 illustrate, by way of example only, a stationary directional dilator 10" according to another aspect of the present invention. The stationary directional dilator 10" includes a stationary dilator 12 and a rotatable electrode structure 14 with an electrode 16 at the distal end. The outer dilator 12 is generally tubular and hollow along its entire length like that shown in FIGS. 16-17 with an inner lumen (not shown, but the same as lumen 32 in FIGS. 3-4) designed to accommodate and enable rotation of the rotatable electrode structure 14. As shown in FIGS. 22-23, the rotatable electrode structure 14 is essentially identical to the embodiment shown and described above with reference to FIGS. 18-19, with the following exceptions. First, the collar member 40 includes a recess 41 having an electrode surface 47 dimensioned to be coupled to a "clamp" or "clip" style electrical connector to establish electrical communication between the intraoperative monitoring system and the stationary directional dilator 10". Second, the electrode marker 48 is broken into two sections 48a (above recess 41) and 48b (below the recess 41), both of which are in alignment with the electrode 16. In the interest of brevity, the other common features and components need not be repeated.

The components forming the stationary directional dilators 10, 10', 10" may be constructed from any number of suitable materials for carrying out the intended purpose of performing directional dilation during intraoperative monitoring. In this regard, all components other than the electrodes (e.g. 16, 18, 46, 47) may be made of plastic, carbon fiber or metal (e.g. aluminum) so long as any such metallic non-electrode components are adequately insulated to prevent unwanted shunting that may otherwise occur. The non-electrode structures (e.g. dilator 12, electrode structure 14, cap member, 19, etc. . . . ) may be manufactured such that the electrodes are separate components fixed onto and/or molded into the respective part or portion of the non-electrode structure, such as where those structures are manufactured from non-conductive material (e.g. plastic, carbon fiber, etc.). Alternatively, if manufactured from a conductive material (e.g. aluminum, etc.), the non-electrode structures may be coated or otherwise treated with insulation to effectively creative the electrodes by covering all surface areas other than those areas intended to serve as electrodes.

The stationary directional dilators 10, 10', 10" of the present invention may be dimensioned according to the intended application. For example, these dilators 10, 10', 10" may be provided having a relatively short length if intended for use in posterior spine surgery procedures where the distances between the skin incision and surgical target site (e.g. disc space), ranging for example from 40 mm to 80 mm. If intended for use in lateral spine surgery, the length will be longer to accommodate the longer distance between the skin incision and the surgical target site, ranging for example from 90 mm to 150 mm. If intended to serve as a sequential dilator within series of sequential dilators, the stationary directional dilators 10, 10', 10" may be provided for each size of the series of sequential dilators or, alternatively, to serve as some but not all of the sequential dilators. Lastly, it will be appreciated that the stationary directional dilators 10, 10', 10" may be dimensioned to serve as the actual working corridor to the surgical target site. If intended for use as a working corridor, the stationary directional dilator may be dimensioned such that the inner lumen to pass the appropriate instruments and/or implants to the surgical target site.

In any of the foregoing embodiments (10, 10', 10"), rotation of the electrode structure 14 may be manual, such as by manually twisting the collar member 40 in between the thumb and forefinger of a user (e.g. surgeon). By looking at the electrode marker 48, the user will be able to tell the direction of the electrode 16 within the patient. Although not shown, the rotation of the electrode structure 14 may also be automated, such as by providing a motor or other transmission mechanism to drive the electrode structure 14 into rotation. Such an automated rotation mechanism may be part of the stationary directional dilators of the type described herein, or may be part of a robotic surgery system which drive the rotation of the electrode 16 relative to the stationary dilator 12. In either case, such an automated rotation mechanism may obviate the need to manually twist the collar member 40 into motion or at least augment the speed of manual rotation. In either event, to accomplish this the intraoperative neuromonitoring system may be used to provide feedback to the motor to selectively rotate the ring member 42 to position the directional electrode 16 in order to determine the direction of the associated nerve or neural structure relative to the distal region of the dilator.

Figure 24:
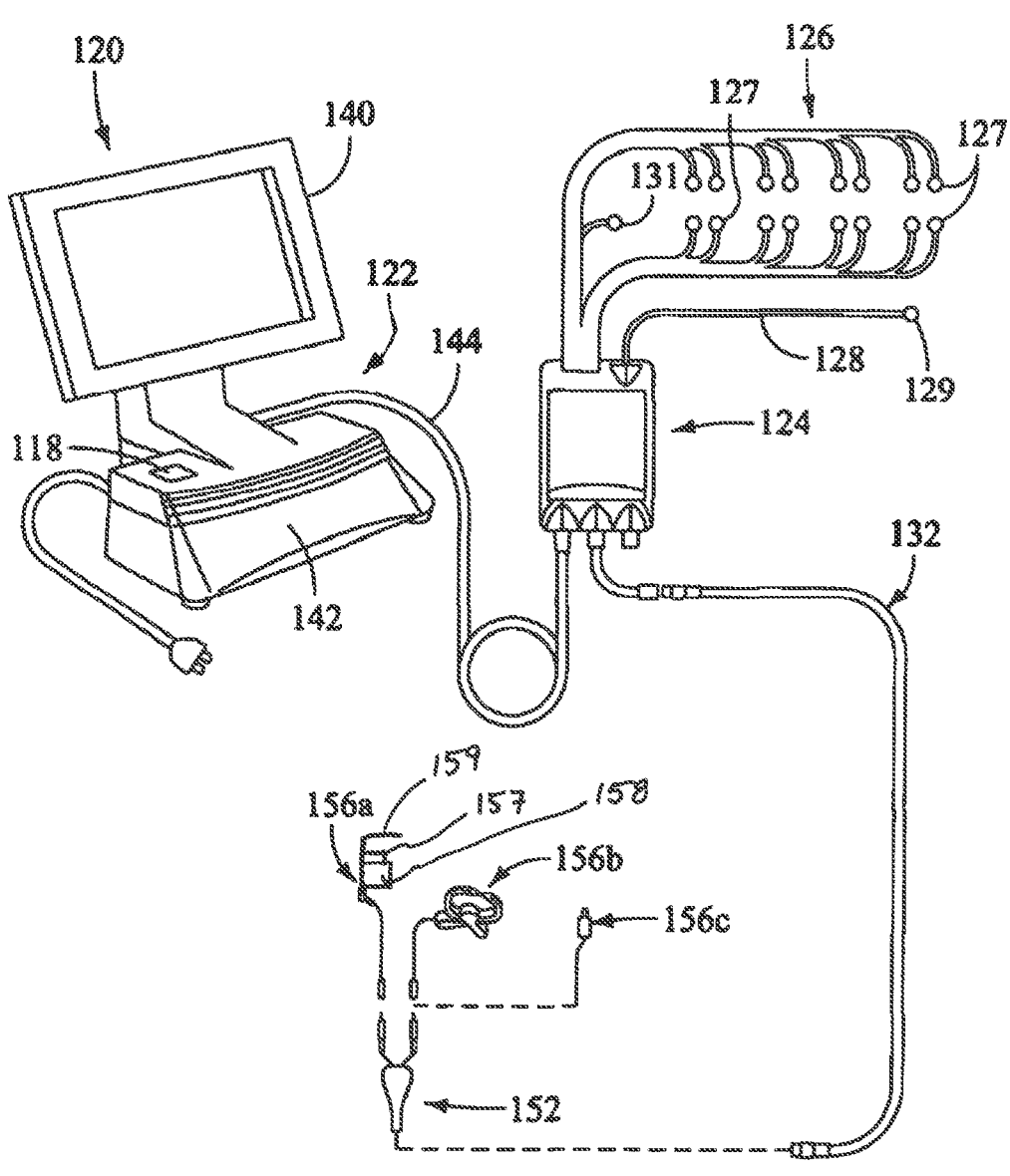
FIG. 24 is a diagram of an exemplary intraoperative monitoring system for use with a stationary directional dilator of the present invention.
Figure 25:
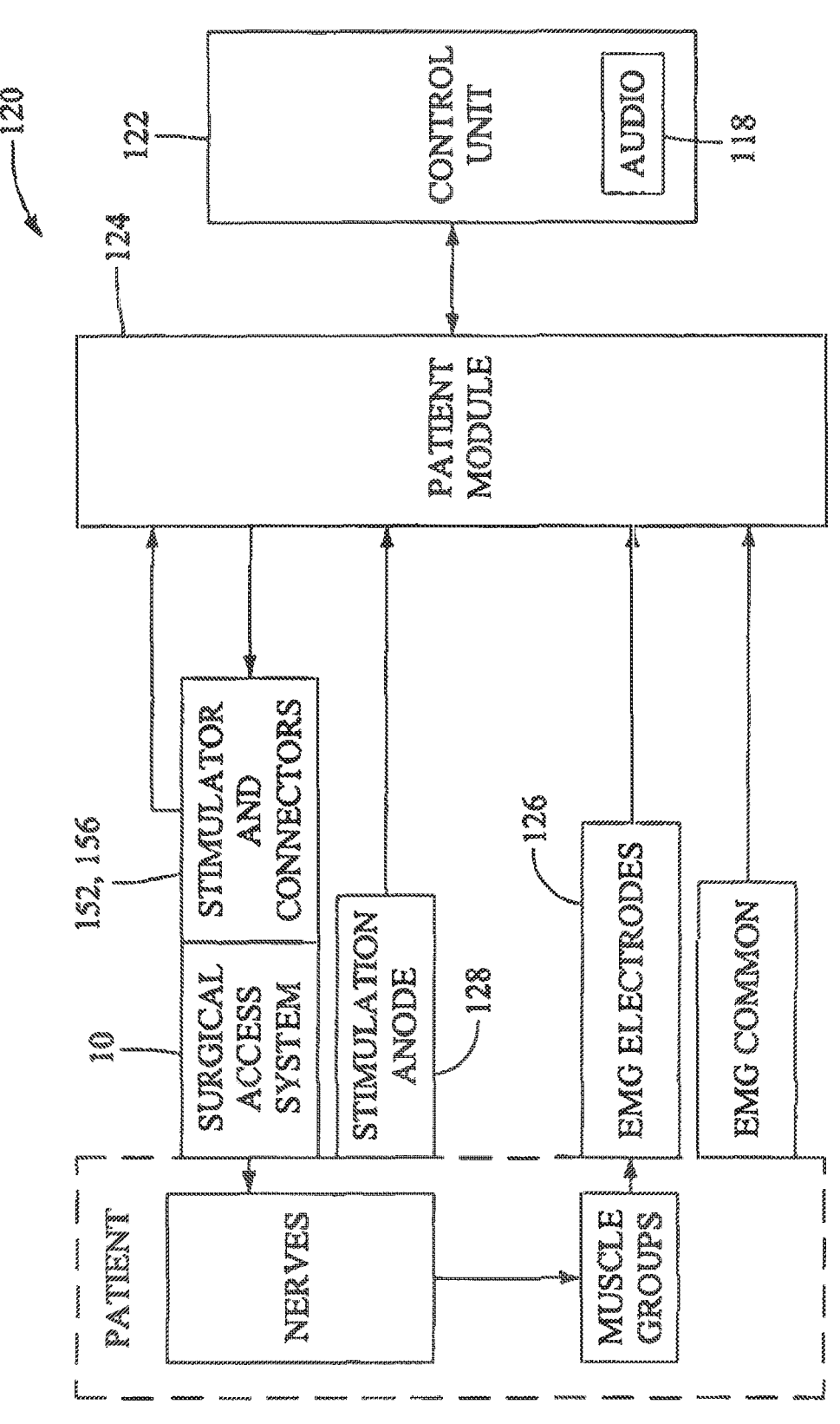
FIG. 25 is a schematic diagram illustrating the functional components of the intraoperative monitoring system set forth in FIG. 24.

FIGS. 24-25 illustrate, by way of example only, a monitoring system 120 of the type disclosed in the '840 patent suitable for use with the stationary directional dilator 10 of the present invention. (Although described in use with dilator 10, it will be appreciated that use with the dilators 10' and 10" will be operate according to the same principles.) The monitoring system 120 includes a control unit 122, a patient module 124, and an EMG harness 126 and return electrode 128 coupled to the patient module 124, and a cable 132 for establishing electrical communication between the patient module 124 and the stationary directional dilator 10 of the present invention. Although not shown, the stationary directional dilator 10 may be used along with various other surgical access instruments to create an operative corridor from a lateral approach through the psoas muscle to a surgical target site in the lumbar spine (e.g. K-wires, sequential dilators (smaller or larger diameter than that of dilator 10), split blade retractors, etc.).

Electrical communication can be achieved by providing, by way of example only, a hand-held stimulation controller 152 capable of selectively providing a stimulation signal (due to the operation of manually operated buttons on the hand-held stimulation controller 152) to one or more connectors 156a, 156b, 156c. The connectors 156a, 156b, 156c are suitable to establish electrical communication between the hand-held stimulation controller 152 and (by way of example only) the stimulation electrode 16 on the stationary directional dilator 10, as well as any electrodes on any other surgical access instruments having electrodes for use in nerve detection and/or proximity.

It will be appreciated that any number different types of connectors 156 may be used depending upon the manner of engaging or coupling to the stationary directional dilator 10. By way of example only, connector 156a is a "plunger" type, connector 156b is a "clip" type, and connector 156c is a "pin" type. Connector 156a has a generally cylindrical contact 157 housed partially within a generally cylindrical body 158 and spring loaded towards an arm member 159. The contact 157 may be moved away from the arm member 159 in order to be placed over an instrument to be electrified (for example electrode 18 of FIGS. 1-2), at which point the contact 157 may be released in order to effectively pinch the instrument in between the contact 157 and arm member 159 to establish the desired electrical contact. Connector 156b includes a pair of arms which are spring loaded towards one another and include at least one electrode such that, when opened and closed over an instrument to be electrified (for example electrode 47 of FIGS. 20-21), the arms effectively pinch the instrument to establish the desired electrical contact. Connector 156c includes a pin which may be introduced into a female electrical connector on the instrument to be electrified.

In order to use the monitoring system 120, at least one of the connectors 156a, 156b and 156c will need to be coupled to the stationary directional dilator 10, such as (by way of example) connecting connector 156a to the electrical coupler 18 in FIG. 1-2 or by connecting connector 156b to the electrode 47 in FIGS. 20-21. The user may thereafter selectively initiate a stimulation signal (preferably, a current signal) from the control unit 122 to the electrode 16 of the stationary directional dilator 10. Stimulating the electrode 16 on the stationary directional dilator 10 before, during and/or after establishing operative corridor will cause nerves that come into close or relative proximity to the surgical access instruments to depolarize, producing a response in a myotome associated with the innervated nerve.

The control unit 122 includes a touch screen display 140 and a base 142, which collectively contain the essential processing capabilities (software and/or hardware) for controlling the monitoring system 120. The control unit 122 may include an audio unit 118 that emits sounds according to a location of a surgical instrument with respect to a nerve. The patient module 124 is connected to the control unit 122 via a data cable 144, which establishes the electrical connections and communications (digital and/or analog) between the control unit 122 and patient module 124. The main functions of the control unit 122 include receiving user commands via the touch screen display 140, activating stimulation electrodes on the surgical access instruments, processing signal data according to defined algorithms, displaying received parameters and processed data, and monitoring system status and report fault conditions.

The touch screen display 140 is preferably equipped with a graphical user interface (GUI) capable of communicating information to the user and receiving instructions from the user. The display 140 and/or base 142 may contain patient module interface circuitry (hardware and/or software) that commands the stimulation sources, receives digitized signals and other information from the patient module 124, processes the EMG responses to extract characteristic information for each muscle group, and displays the processed data to the operator via the display 140.

In one aspect, the monitoring system 120 is capable of determining nerve direction relative to the stationary directional dilator 10 before, during and/or following the creation of an operative corridor to a surgical target site. Monitoring system 120 accomplishes this by having the control unit 122 and patient module 124 cooperate to send electrical stimulation signals to the electrode 16 on the stationary directional dilator 10.

Depending upon the location of the stationary directional dilator 10 within a patient (and more particularly, to any neural structures), the stimulation signals may cause nerves adjacent to or in the general proximity of the dilator 10 to depolarize. This causes muscle groups to innervate and generate EMG responses, which can be sensed via the EMG harness 126. By monitoring the myotomes associated with the nerves (via the EMG harness 126 and recording electrodes 127) and assessing the resulting EMG responses (via the control unit 122), the system 120 is capable of detecting the presence of such nerves.

The stationary directional dilator 10 of the present invention allows a user to determine the direction to nerves. To do so, the user need simply hold the dilator 12 in a generally stationary position while rotating the electrode 16 as the stimulation signal is being emitted to the surrounding tissue. The closer the nerve is to the electrode 16, the lower the electrical stimulation (e.g. current) required to innervate the nerve. As such, the user may simply rotate the electrode 16 to identify the point in its rotation relative to the dilator 12 at which the stimulation signal required to innervate the nerve is the lowest. This is facilitated by visualizing the electrode marker 48, given the location of the electrode 16 within the patient. This point is the direction of the nerve relative to the stationary dilator 12.

By determining the direction to adjacent nerves, the stationary directional dilator 10 provides the ability to actively negotiate around or past such nerves to safely and reproducibly form the operative corridor to a particular surgical target site. In spinal surgery, for example, this is particularly advantageous in that the stationary directional dilator 10 may be particularly suited for detecting the presence and direction of nerves during the process of establishing an operative corridor through the psoas muscle to an intervertebral target site in the lumbar spine.

Any of the features or attributes of the above the above described embodiments and variations can be used in combination with any of the other features and attributes of the above described embodiments and variations as desired. Various modifications, additions and other alternative embodiments are possible without departing from the true scope and spirit. The embodiments presented herein were chosen and described to provide an illustration of various principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

What is claimed is:

1. A stationary directional dilator, comprising:
a first tubular structure having a first proximal end, a first distal end, and an inner lumen extending between said first proximal end and said first distal end; and
a second structure rotatably coupled to said first tubular structure, said second structure having a second proximal end, a second distal end, and an electrode located proximate said second distal end and configured to transmit an electric signal to surrounding tissue when said electrode is in electrical communication with an intraoperative monitor,
wherein said second structure is dimensioned to be rotated relative to the first tubular structure to thereby rotate said electrode in order to determine a direction of nerves located in said tissue relative to said first tubular structure as said first tubular structure and said second structure are advanced through said tissue; and
wherein the first tubular structure defines a circumferential surface proximate the first proximal end and further defines a plurality of circumferential apertures through the circumferential surface through which a user may rotate the second proximal end of the second structure relative to said first tubular structure,
wherein said second structure includes a collar at said second proximal end, a ring at said second distal end, and a plurality of struts extending between said collar and said ring, wherein said electrode is disposed on said ring.

2. The stationary directional dilator of claim 1, wherein said first proximal end of said first tubular structure is dimensioned to receive at least a portion of said second proximal end of said second structure.

3. The stationary directional dilator of claim 1, wherein the ring is adjacent to the first distal end of the first tubular structure, and wherein said electrode is disposed on said ring.

4. The stationary directional dilator of claim 1, wherein the collar is dimensioned to be selectively rotated by the user relative to the first tubular structure in order to rotate said electrode.

5. The stationary directional dilator of claim 4, wherein said collar is housed at least partially within the first proximal end of said first tubular structure.

6. The stationary directional dilator of claim 4, wherein said collar is positioned adjacent to the first proximal end of said first tubular structure.

7. The stationary directional dilator of claim 1, further comprising an electrical coupler in electrical communication to the electrode, the electrical coupler being configured to establish the electrical communication between the electrode and the intraoperative monitor when said electrical coupler is connected to the intraoperative monitor.

8. The stationary directional dilator of claim 1, further comprising:
a cap dimensioned to retain the collar at said second proximal end of said second structure within said first proximal end of said first tubular structure; and
an electrical coupler extending from said cap and in electrical communication to the electrode, the electrical coupler being configured to establish the electrical communication between the electrode and the intraoperative monitor when said electrical coupler is connected to the intraoperative monitor.

9. The stationary directional dilator of claim 1, wherein said electrode is configured to be rotated manually by the user moving said second structure relative to said first tubular structure.

10. The stationary directional dilator of claim 1, wherein at least one of said first tubular structure and said second structure is configured with at least one of audio and visual emission capabilities to transmit an audio indicia or a visual indicia to the user to communicate information pertaining to distance and direction of nerve tissue relative to said first tubular structure.

11. A method comprising:

advancing a first tubular dilator through tissue in a human subject;

rotating, through two or more circumferential apertures at a first proximal end of the first tubular dilator, a second structure rotatably coupled to and disposed at least partially within said first tubular dilator such that an electrode disposed on a second distal end of said second structure emits an electrical signal into said tissue; and iteratively rotating said second structure relative to said first tubular dilator until said electrical signal emitted from said electrode causes nerve tissue to innervate based on the electrical signal, wherein said second structure includes a collar at a second proximal end, a ring at said second distal end, and a plurality of struts extending between said collar and said ring, wherein said electrode is disposed on said ring.

12. The method of claim 11, wherein said electrode is coupled to an electromyographic intraoperative monitor.

13. The method of claim 11, wherein said step of iteratively rotating is performed manually by a user moving said second structure relative to said first tubular dilator.

14. The method of claim 11, further comprising:

equipping at least one of said first tubular dilator and said second structure with at least one of audio and visual emission capabilities; and communicating to a user at least one of audio and visual information pertaining to at least one of distance and direction of the nerve tissue relative to said first tubular dilator.

*  *  *  *  *